(12) United States Patent
Fischer et al.

(10) Patent No.: US 9,815,909 B2
(45) Date of Patent: Nov. 14, 2017

(54) READILY ISOLATED BISPECIFIC ANTIBODIES WITH NATIVE IMMUNOGLOBULIN FORMAT

(71) Applicant: NovImmune S.A., Geneva (CH)

(72) Inventors: Nicolas Fischer, Geneva (CH); Giovanni Magistrelli, Cessy (FR); Francois Rousseau, Collonges sous Saleve (FR); Krzysztof Masternak, Mollens (CH); Pauline Malinge, Cernex (FR)

(73) Assignee: NOVIMMUNE S.A. (CH)

( * ) Notice: Subject to any disclaimer, the term of this patent is extended or adjusted under 35 U.S.C. 154(b) by 284 days.

(21) Appl. No.: 13/798,485

(22) Filed: Mar. 13, 2013

(65) Prior Publication Data

US 2014/0051833 A1  Feb. 20, 2014

Related U.S. Application Data

(60) Provisional application No. 61/610,141, filed on Mar. 13, 2012.

(51) Int. Cl.
| | | |
|---|---|---|
| *C07K 16/24* | (2006.01) | |
| *C07K 16/28* | (2006.01) | |
| *C07K 16/46* | (2006.01) | |

(52) U.S. Cl.
CPC .......... *C07K 16/468* (2013.01); *C07K 16/244* (2013.01); *C07K 16/2809* (2013.01); *C07K 2317/31* (2013.01)

(58) Field of Classification Search
CPC  B01D 15/388; B01D 15/3804; C07K 16/244; C07K 16/2809; C07K 16/468; C07K 2317/31
See application file for complete search history.

(56) References Cited

FOREIGN PATENT DOCUMENTS

| WO | WO 01/77342 A1 | 10/2001 |
|---|---|---|
| WO | WO 2006/008548 A2 | 1/2006 |
| WO | WO 2007/147901 A1 | 12/2007 |

OTHER PUBLICATIONS

Golay et al., Archives of Biochemistry and Biophysics 526: 146-153, 2012.*
Yu et al., Investigative Ophthalmology & Visual Science 49(2): 522-527, Feb. 2008.*
Stancovski et al., PNAS 88: 8691-8695, 1991.*
Rouet et al., Nature Biotechnology 32(2): 136-137, Feb. 2014.*
"http://www.captureselect.com/shopfiles/upload/files/Product_Sheet_CaptureSelect_IgG-CH1.pdf" Mar. 9, 2011, pp. 1-4; retrieved on Jun. 16, 2011.

* cited by examiner

*Primary Examiner* — Phuong Huynh
(74) *Attorney, Agent, or Firm* — Cooley LLP; Ivor Elrifi; Cynthia Kozakiewicz

(57) ABSTRACT

The invention relates to antigen-binding proteins or antibodies having heterodimers of heavy chains, i.e., two immunoglobulin heavy chains that differ by at least one or two amino acid(s) that allows for isolation of the antigen-binding protein based on a differential affinity of an immunoglobulin heavy chain and a modified/mutated immunoglobulin heavy chain toward an affinity reagent. The invention also relates antigen-binding proteins, including bispecific antibodies, having IgG CH1 regions with different affinities with respect to affinity reagent(s) that allows rapid isolation by differential binding of the IgG regions to the affinity reagent(s).

10 Claims, 10 Drawing Sheets

FIGURE 1

| species | Mab | Isotype | specificity |
|---|---|---|---|
| human | NI0001 | humanized IgG1 | +++ |
| | NI0701 | IgG1 | +++ |
| hamster | HM 79 | IgG | +++ |
| mouse | W6-32 | IgG2a | - |
| | IV.3 | IgG2b | - |
| rat | GK 1.5 | IgG2b | - |
| | MAB 35 | IgG1 | - |
| | 1F7 | IgG2a | - |
| | 25F10 | IgG1 | - |

| Mutant | Mutation(s) |
|--------|-------------|
| M2 | 40 : S --> T    47 : T --> S |
| M2ST | 40 : S --> T |
| M2TS | 47 : T --> S |
| M3 | 40 : S --> T    45 : A --> S    47 : T --> S |

SEQUENCE LISTING

<160> NUMBER OF SEQ ID NOS: 18

<210> SEQ ID NO 1
<211> LENGTH: 98
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 2
<211> LENGTH: 98
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 3
<211> LENGTH: 98
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 5
<211> LENGTH: 99
<212> TYPE: PRT
<213> ORGANISM: Mesocricetus auratus

<400> SEQUENCE: 5

Ala Thr Thr Thr Ala Pro Ser Val Tyr Pro Leu Ala Pro Ala Cys Asp
1               5                   10                  15

Ser Thr Thr Ser Thr Thr Asp Thr Val Thr Leu Gly Cys Leu Val Lys
            20                  25                  30

Gly Tyr Phe Pro Glu Pro Val Thr Val Ser Trp Asn Ser Gly Ala Leu
        35                  40                  45

Thr Ser Gly Val His Thr Phe Pro Ser Val Leu His Ser Gly Leu Tyr
    50                  55                  60

Ser Leu Ser Ser Ser Val Thr Val Pro Ser Ser Thr Trp Pro Lys Gln
65                  70                  75                  80

```
Pro Ile Thr Cys Asn Val Ala His Pro Ala Ser Ser Thr Lys Val Asp
                85                  90                  95

Lys Lys Ile

<210> SEQ ID NO 6
<211> LENGTH: 97
<212> TYPE: PRT
<213> ORGANISM: Mus musculus

<400> SEQUENCE: 6

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
                35                  40                  45

Gly Val His Thr Phe Pro Ala Val Leu Glu Ser Asp Leu Tyr Thr Leu
            50                  55                  60

Ser Ser Ser Val Thr Val Pro Ser Ser Pro Arg Pro Ser Glu Thr Val
65              70                  75                  80

Thr Cys Asn Val Ala His Pro Ala Ser Ser Thr Lys Val Asp Lys Lys
                85                  90                  95

Ile

<210> SEQ ID NO 7
<211> LENGTH: 97
<212> TYPE: PRT
<213> ORGANISM: Mus musculus

<400> SEQUENCE: 7

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
                35                  40                  45

Gly Val His Thr Phe Pro Ala Val Leu Gln Ser Asp Leu Tyr Thr Leu
            50                  55                  60

Ser Ser Ser Val Thr Val Thr Ser Ser Thr Trp Pro Ser Gln Ser Ile
65              70                  75                  80

Thr Cys Asn Val Ala His Pro Ala Ser Ser Thr Lys Val Asp Lys Lys
                85                  90                  95

Ile

<210> SEQ ID NO 8
<211> LENGTH: 97
<212> TYPE: PRT
<213> ORGANISM: Mus musculus

<400> SEQUENCE: 8

Ala Lys Thr Thr Pro Pro Ser Val Tyr Pro Leu Ala Pro Gly Cys Gly
1               5                   10                  15

Asp Thr Thr Gly Ser Ser Val Thr Ser Gly Cys Leu Val Lys Gly Tyr
                20                  25                  30

Phe Pro Glu Pro Val Thr Val Thr Trp Asn Ser Gly Ser Leu Ser Ser
                35                  40                  45
```

```
Ser Val His Thr Phe Pro Ala Leu Leu Gln Ser Gly Leu Tyr Thr Met
     50                  55                  60

Ser Ser Ser Val Thr Val Pro Ser Ser Thr Trp Pro Ser Gln Thr Val
 65                  70                  75                  80

Thr Cys Ser Val Ala His Pro Ala Ser Ser Thr Thr Val Asp Lys Lys
                     85                  90                  95

Leu

<210> SEQ ID NO 9
<211> LENGTH: 97
<212> TYPE: PRT
<213> ORGANISM: Mus musculus

<400> SEQUENCE: 9

Ala Lys Thr Thr Ala Pro Ser Val Tyr Pro Leu Ala Pro Val Cys Gly
 1               5                  10                  15

Gly Thr Thr Gly Ser Ser Val Thr Leu Gly Cys Leu Val Lys Gly Tyr
                 20                  25                  30

Phe Pro Glu Pro Val Thr Leu Thr Trp Asn Ser Gly Ser Leu Ser Ser
             35                  40                  45

Gly Val His Thr Phe Pro Ala Leu Leu Gln Ser Gly Leu Tyr Thr Leu
     50                  55                  60

Ser Ser Ser Val Thr Val Thr Ser Asn Thr Trp Pro Ser Gln Thr Ile
 65                  70                  75                  80

Thr Cys Asn Val Ala His Pro Ala Ser Ser Thr Lys Val Asp Lys Lys
                     85                  90                  95

Ile

<210> SEQ ID NO 10
<211> LENGTH: 97
<212> TYPE: PRT
<213> ORGANISM: Mus musculus

<400> SEQUENCE: 10

Ala Thr Thr Thr Ala Pro Ser Val Tyr Pro Leu Val Pro Gly Cys Ser
 1               5                  10                  15

Asp Thr Ser Gly Ser Ser Val Thr Leu Gly Cys Leu Val Lys Gly Tyr
                 20                  25                  30

Phe Pro Glu Pro Val Thr Val Lys Trp Asn Tyr Gly Ala Leu Ser Ser
             35                  40                  45

Gly Val Arg Thr Val Ser Ser Val Leu Gln Ser Gly Phe Tyr Ser Leu
     50                  55                  60

Ser Ser Leu Val Thr Val Pro Ser Ser Thr Trp Pro Ser Gln Thr Val
 65                  70                  75                  80

Ile Cys Asn Val Ala His Pro Ala Ser Lys Thr Glu Leu Ile Lys Arg
                     85                  90                  95

Ile

<210> SEQ ID NO 11
<211> LENGTH: 97
<212> TYPE: PRT
<213> ORGANISM: Rattus norvegicus

<400> SEQUENCE: 11

Ala Glu Thr Thr Ala Pro Ser Val Tyr Pro Leu Ala Pro Gly Thr Ala
 1               5                  10                  15

Leu Lys Ser Asn Ser Met Val Thr Leu Gly Cys Leu Val Lys Gly Tyr
```

```
                    20                  25                  30

Phe Pro Glu Pro Val Thr Val Thr Trp Asn Ser Gly Ala Leu Ser Ser
                35                  40                  45

Gly Val His Thr Phe Pro Ala Val Leu Gln Ser Gly Leu Tyr Thr Leu
            50                  55                  60

Thr Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile

<210> SEQ ID NO 12
<211> LENGTH: 97
<212> TYPE: PRT
<213> ORGANISM: Rattus norvegicus

<400> SEQUENCE: 12

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
                20                  25                  30

Phe Pro Glu Pro Val Thr Val Thr Trp Asn Ser Gly Ala Leu Ser Ser
                35                  40                  45

Gly Val His Thr Phe Pro Ala Val Leu Gln Ser Gly Leu Tyr Thr Leu
            50                  55                  60

Thr Ser Ser Val Thr Val Pro Ser Ser Thr Trp Ser Ser Gln Ala Val
65                  70                  75                  80

Thr Cys Asn Val Ala His Pro Ala Ser Ser Thr Lys Val Asp Lys Lys
                85                  90                  95

Ile

<210> SEQ ID NO 13
<211> LENGTH: 95
<212> TYPE: PRT
<213> ORGANISM: Rattus norvegicus

<400> SEQUENCE: 13

Ala Gln Thr Thr Ala Pro Ser Val Tyr Pro Leu Ala Pro Gly Cys Gly
1               5                   10                  15

Asp Thr Thr Ser Ser Thr Val Thr Leu Gly Cys Leu Val Lys Gly Tyr
                20                  25                  30

Phe Pro Glu Pro Val Thr Val Thr Trp Asn Ser Gly Ala Leu Ser Ser
                35                  40                  45

Asp Val His Thr Phe Pro Ala Val Leu Gln Ser Gly Leu Tyr Thr Leu
            50                  55                  60

Thr Ser Ser Val Thr Ser Ser Thr Trp Pro Ser Gln Thr Val Thr Cys
65                  70                  75                  80

Asn Val Ala His Pro Ala Ser Ser Thr Lys Val Asp Lys Lys Val
                85                  90                  95

<210> SEQ ID NO 14
<211> LENGTH: 97
<212> TYPE: PRT
<213> ORGANISM: Rattus norvegicus

<400> SEQUENCE: 14

Ala Arg Thr Thr Ala Pro Ser Val Tyr Pro Leu Val Pro Gly Cys Ser
```

```
                1               5                   10                  15
Gly Thr Ser Gly Ser Leu Val Thr Leu Gly Cys Leu Val Lys Gly Tyr
                20                  25                  30

Phe Pro Glu Pro Val Thr Val Lys Trp Asn Ser Gly Ala Leu Ser Ser
                35                  40                  45

Gly Val His Thr Phe Pro Ala Val Leu Gln Ser Gly Leu Tyr Thr Leu
                50                  55                  60

Ser Ser Ser Val Thr Val Pro Ser Ser Thr Trp Ser Ser Gln Thr Val
65                  70                  75                  80

Thr Cys Ser Val Ala His Pro Ala Thr Lys Ser Asn Leu Ile Lys Arg
                    85                  90                  95

Ile

<210> SEQ ID NO 15
<211> LENGTH: 98
<212> TYPE: PRT
<213> ORGANISM: Artificial Sequence
<220> FEATURE:
<223> OTHER INFORMATION: chemically synthesized

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Thr Trp Asn Ser Gly Ala Leu Ser Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val

<210> SEQ ID NO 16
<211> LENGTH: 98
<212> TYPE: PRT
<213> ORGANISM: Artificial Sequence
<220> FEATURE:
<223> OTHER INFORMATION: chemically synthesized

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Thr Trp Asn Ser Gly Ala Leu Ser Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                    85                  90                  95

Thr Val
```

```
<210> SEQ ID NO 17
<211> LENGTH: 98
<212> TYPE: PRT
<213> ORGANISM: Artificial Sequence
<220> FEATURE:
<223> OTHER INFORMATION: chemically synthesized

<400> SEQUENCE: 17

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 18
<211> LENGTH: 98
<212> TYPE: PRT
<213> ORGANISM: Artificial Sequence
<220> FEATURE:
<223> OTHER INFORMATION: chemically synthesized

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val
```

READILY ISOLATED BISPECIFIC ANTIBODIES WITH NATIVE IMMUNOGLOBULIN FORMAT

RELATED APPLICATIONS

This application claims the benefit of U.S. Provisional Application No. 61/610,141, filed Mar. 13, 2012. The contents of this application are hereby incorporated by reference in their entirety.

INCORPORATION OF SEQUENCE LISTING

The contents of the text file named "NOVI027001US_Sub4SL.txt", which was created on Nov. 24, 2015 and is 20.0 KB in size, are hereby incorporated by reference in their entirety.

FIELD OF INVENTION

The invention concerns antigen-binding proteins or antibodies having heterodimers of heavy chains, i.e., two immunoglobulin heavy chains that differ by at least one amino acid that allows for the isolation of the antigen-binding protein based on a differential affinity of an immunoglobulin heavy chain and a modified or mutated immunoglobulin heavy chain toward an affinity reagent. The invention also concerns antigen-binding proteins or antibodies having heterodimers of heavy chains, i.e., two immunoglobulin heavy chains that differ by at least two amino acids that allow for the isolation of the antigen-binding protein based on a differential affinity of an immunoglobulin heavy chain and a modified or mutated immunoglobulin heavy chain toward an affinity reagent. The invention also concerns antigen-binding proteins (including bispecific antibodies) that have IgG CH1 regions with different affinities with respect to affinity reagent that allows rapid isolation by differential binding of the IgG regions to this affinity reagent.

BACKGROUND OF THE INVENTION

Antibodies are multifunctional molecules carrying a unique binding specificity for a target antigen or multiple targets and having the capacity to interact with the immune system via mechanisms that are antigen-independent. Many currently used biological therapeutics for cancer are monoclonal antibodies directed against antigens that are typically overexpressed on the targeted cancer cell. When such antibodies bind tumor cells, they may trigger antibody-dependent cellular cytotoxicity (ADCC) or complement-dependent cytotoxicity (CDC). Unfortunately, cancerous cells often develop mechanisms to suppress these normal immune responses. In addition, targeting or neutralizing a single protein is not always sufficient to achieve efficacy in certain diseases which limits the therapeutic use of monoclonal antibodies. It is increasingly clear that in a number of indications neutralizing one component of a biological system is not sufficient to achieve efficacy.

Accordingly, there remains a need for a bispecific antibody format, in particular for therapeutic applications, that minimizes some or all of the disadvantages mentioned above.

SUMMARY OF THE INVENTION

The invention is based at least in part on employing two immunoglobulin CH1 heavy chain constant domain sequences that differ by at least one amino acid in a bispecific antigen-binding protein and form a heterodimer. The amino acid difference results in an improved ability to quickly and effectively isolate the heteromeric protein from homodimers, because the difference results in a differential ability of the CH1 domain sequences to bind the Capture-Select® IgG-CH1 (BAC BV) affinity reagent. In one aspect, an antigen-binding protein is provided, comprising a first and a second polypeptide, the first polypeptide comprising, from N-terminal to C-terminal, a first antigen-binding region that selectively binds a first antigen, followed by a constant region that comprises a first CH1 region of a human IgG selected from IgG1 (SEQ ID NO: 1), IgG2 (SEQ ID NO: 2), IgG3 (SEQ ID NO: 3), IgG4 (SEQ ID NO: 4), and a combination thereof; and, a second polypeptide comprising, from N-terminal to C-terminal, a second antigen-binding region that selectively binds a second antigen, followed by a constant region that comprises a second CH1 region of a human IgG selected from IgG1, IgG2, IgG3, IgG4, and a combination thereof, wherein the second CH1 region comprises a modification that reduces or eliminates binding of the second CH1 domain to the CaptureSelect® IgG-CH1 affinity reagent.

The invention is also based at least in part on employing two immunoglobulin CH1 heavy chain constant domain sequences that differ by at least two amino acids in a bispecific antigen-binding protein and form a heterodimer. The two amino acid difference results in an improved ability to quickly and effectively isolate the heteromeric protein from homodimers, because the difference results in a differential ability of the CH1 domain sequences to bind the CaptureSelect® IgG-CH1 (BAC BV) affinity reagent. In one aspect, an antigen-binding protein is provided, comprising a first and a second polypeptide, the first polypeptide comprising, from N-terminal to C-terminal, a first antigen-binding region that selectively binds a first antigen, followed by a constant region that comprises a first CH1 region of a human IgG selected from IgG1 (SEQ ID NO: 1), IgG2 (SEQ ID NO: 2), IgG3 (SEQ ID NO: 3), IgG4 (SEQ ID NO: 4), and a combination thereof; and, a second polypeptide comprising, from N-terminal to C-terminal, a second antigen-binding region that selectively binds a second antigen, followed by a constant region that comprises a second CH1 region of a human IgG selected from IgG1, IgG2, IgG3, IgG4, and a combination thereof, wherein the second CH1 region comprises a modification that reduces or eliminates binding of the second CH1 domain to the CaptureSelect® IgG-CH1 affinity reagent.

In one embodiment, the second CH1 region comprises mutations modifying residues S40 and T47, according to the IMGT exon numbering system (IMGT®, the international ImMunoGeneTics information system®).

In some embodiments, the second CH1 region comprises the S40T and T47S modifications. As used herein, an "S40T" mutation is one in which the wild-type residue, serine, at position 40 is replaced with a threonine (i.e., S→T mutation at residue 40). Likewise, as used herein, a "T47S" mutation is one in which the wild-type residue, threonine, at position 40 is replaced with a serine (i.e., T→S mutation at residue 47).

In specific embodiments, the second CH1 region is selected from SEQ ID NO: 15, SEQ ID NO: 16, SEQ ID NO: 17, and SEQ ID NO: 18.

In one embodiment, the second CH1 region is or is derived from a modified human IgG1 (SEQ ID NO: 15).

In one embodiment, the second CH1 region is or is derived from a modified human IgG2 (SEQ ID NO: 16).

In one embodiment, the second CH1 region is from a modified human IgG3 (SEQ ID NO: 17).

In one embodiment, the second CH1 region is from a modified human IgG4 (SEQ ID NO: 18).

In one embodiment, the CH1 domain is a chimeric domain that comprises sequences of two or more of human IgG1, human IgG2, human IgG3 and human IgG4.

In one embodiment, the CH1 domain is from human IgG1, human IgG2, human IgG3, or human IgG4, and the antigen-binding protein further comprises a CH2 domain and a CH3 domain, wherein the CH2 domain and the CH3 domain are independently selected from the group consisting of a human IgG1 CH2 or CH3 domain, a human IgG2 CH2 or CH3 domain, a human IgG3 CH2 or CH3 domain, a human IgG4 CH2 or CH3 domain.

In one embodiment, the antigen-binding protein further comprises an immunoglobulin light chain.

In other embodiment the immunoglobulin light chain is selected from a human lambda and a human kappa light chain.

In one embodiment, the first and the second antigen-binding regions each comprise at least one complementarity determining region (CDR). In another embodiment, the first and the second antigen-binding regions each comprise at least two CDRs. In another embodiment, the first and the second antigen-binding regions each comprise each comprise three CDRs. In a specific embodiment, the CDRs are from an immunoglobulin heavy chain. In another specific embodiment, the heavy chain is a human heavy chain.

In one embodiment, the first antigen-binding region comprises a first immunoglobulin heavy chain variable domain, and the second antigen-binding region comprises a second immunoglobulin heavy chain variable domain.

In one embodiment, the first and the second immunoglobulin heavy chain variable domains independently comprise a human CDR, a mouse CDR, a rat CDR, a rabbit CDR, a monkey CDR, an ape CDR, a synthetic CDR, and/or a humanized CDR. In one embodiment, the CDR is human and is somatically mutated.

In one embodiment, the first and the second immunoglobulin heavy chain variable domain comprise a human framework region (FR). In one embodiment, the human FR is a somatically mutated human FR.

In one embodiment, the first and/or the second antigen-binding regions are obtained by screening a phage library comprising antibody variable regions for reactivity toward an antigen of interest.

In another embodiment, the first and/or the second antigen-binding regions are obtained by immunizing a non-human animal such as a mouse, a rat, a rabbit, a monkey, or an ape with an antigen of interest and identifying an antibody variable region nucleic acid sequence encoding variable region specific for the antigen of interest.

In another specific embodiment, one or more human immunoglobulin variable region genes are present in the non-human animal extrachromosomally, as a replacement at an endogenous immunoglobulin locus, or as a transgene randomly integrated into the genome of the non-human animal. In one embodiment, the first and/or the second antigen-binding regions are obtained from a hybridoma or a quadroma, in another embodiment from screening immune cells of an immunized non-human animal using cell sorting.

In one embodiment, the antigen-binding protein is a bispecific antibody. In one embodiment, the bispecific antibody is a fully human bispecific antibody and has an affinity for each epitope, independently, in the micromolar, nanomolar, or picomolar range.

In one embodiment, the antigen-binding protein is non-immunogenic or substantially non-immunogenic in a human. In a specific embodiment, the antigen-binding protein lacks a non-native human T-cell epitope. In one embodiment, the modification of the CH1 region is non-immunogenic or substantially non-immunogenic in a human.

In one embodiment, the antigen-binding protein comprises a heavy chain, wherein the heavy chain is non-immunogenic or substantially non-immunogenic in a human.

In one embodiment, the heavy chain has an amino acid sequence that does not contain a non-native T-cell epitope. In one embodiment, the heavy chain comprises an amino acid sequence whose proteolysis cannot form an amino acid sequence of about 9 amino acids that is immunogenic in a human. In a specific embodiment, the human is a human being treated with the antigen-binding protein. In one embodiment, the heavy chain comprises an amino acid sequence whose proteolysis cannot form an amino acid sequence of about 13 to about 17 amino acids that is immunogenic in a human. In a specific embodiment, the human is a human being treated with the antigen-binding protein.

In one aspect, the invention provides isolated multispecific antibodies having more than one antigen binding specificity, wherein the multispecific antibody include at least (i) a first polypeptide comprising a first variable region that binds a first epitope and an immunoglobulin constant region that comprises a first CH1 region of a human IgG selected from IgG1, IgG2, IgG3 and IgG4, and (ii) a second polypeptide comprising a second region that binds a second epitope and an immunoglobulin constant region that comprises a second CH1 region of a human IgG selected from IgG1, IgG2, IgG3 and IgG4, wherein the first and second epitopes are different epitopes, and wherein at least one of the first and second CH1 regions comprises a modification that reduces or eliminates binding of the second CH1 domain to the CaptureSelect®

IgG-CH1 affinity reagent, or any affinity reagent targeting the human IgG1, IgG2, IgG3 and IgG4 CH1 domain.

The invention also provides heterodimeric bispecific antigen-binding proteins that include (a) a first polypeptide comprising, from N-terminal to C-terminal a first epitope-binding region that selectively binds a first epitope and an immunoglobulin constant region that comprises a first CH1 region of a human IgG selected from IgG1, IgG2, IgG3 and IgG4; and, b) a second polypeptide comprising, from N-terminal to C-terminal, a second epitope-binding region that selectively binds a second epitope and an immunoglobulin constant region that comprises a second CH1 region of a human IgG selected from IgG1, IgG2, IgG3 and IgG4, wherein the second CH1 region comprises a modification that reduces or eliminates binding of the second CH1 domain to the CaptureSelect® IgG-CH1 affinity reagent, or any affinity reagent targeting the human IgG1, IgG2, IgG3 and IgG4 CH1 domain.

In some embodiments of the multispecific antibodies, e.g., heterodimeric bispecific antigen-binding proteins, the first polypeptide and the second polypeptide comprise human IgG heavy chains or are derived from human IgG heavy chains. In some embodiments, the multispecific antibodies, e.g., heterodimeric bispecific antigen-binding proteins, also include an immunoglobulin light chain. In some embodiments of the multispecific antibodies, e.g., heterodimeric bispecific antigen-binding proteins, the immunoglobulin light chain is a human immunoglobulin light chain or is derived from a human immunoglobulin light chain. In some embodiments of the multispecific antibodies, e.g., heterodimeric bispecific antigen-binding proteins, the first and the second polypeptides each are human IgG1 heavy chains or are derived from human IgG1 heavy chains. In some embodiments of the multispecific antibodies, e.g., heterodimeric bispecific antigen-binding proteins, the second CH1 region comprises the modification. In some embodiments of the multispecific antibodies, e.g., heterodimeric bispecific antigen-binding proteins, the modification in the second CH1 domain include a mutation modifying S40 in the IMGT® exon numbering system, a mutation modifying T47 in the IMGT® exon numbering system or a combination thereof In some embodiments of the multispecific antibodies, e.g., heterodimeric bispecific antigen-binding proteins, the modification in the second CH1 domain comprises an S40T mutation in the IMGT® exon numbering system, a T47S mutation in the IMGT® exon numbering system or a combination thereof. In some embodiments of the multispecific antibodies, e.g., heterodimeric bispecific antigen-binding proteins, the first CH1 domain of the bispecific antibody, the second CH1 domain or both the first and second CH1 domains are non-immunogenic or substantially non-immunogenic in a human.

In one aspect, a method for making a bispecific antibody is provided, comprising: obtaining a nucleic acid sequence encoding a first immunoglobulin heavy chain comprising a first variable domain that recognizes a first epitope, wherein the first immunoglobulin heavy chain comprises an IgG1, IgG2, IgG3 or IgG4 isotype constant domain; obtaining a second nucleic acid sequence encoding a second immunoglobulin heavy chain comprising a second variable domain that recognizes a second epitope, wherein the second immunoglobulin heavy chain comprises an IgG1, IgG2, IgG3 or IgG4 isotype constant domain, or a chimeric isotype constant domain thereof, that comprises a modification in its CH1 domain that eradicates or reduces binding to the CaptureSelect® IgG-CH1 affinity reagent; obtaining a third nucleic acid sequence encoding an immunoglobulin a light chain that pairs with the first and the second immunoglobulin heavy chain; introducing the first, second, and third nucleic acid sequences into a mammalian cell; allowing the cell to express an immunoglobulin, and isolating the immunoglobulin using the CaptureSelect® IgG-CH1 affinity reagent.

In one embodiment, the cell is selected from a CHO, COS, 293, HeLa, and a retinal cell expressing a viral nucleic acid sequence (e.g., a PERC.6™ cell).

In one aspect, a method for making a bispecific antibody is provided, comprising a step of isolating from a disrupted cell or a mixture of antibodies a bispecific antibody having differentially modified IgG1, IgG2, IgG3 or IgG4 CH1 domains, wherein the differentially modified CH1 domains are non-immunogenic or substantially non-immunogenic in a human, and wherein the modification results in a bispecific antibody with heterodimeric heavy chains whose monomers have a differential affinity for an affinity reagent, and the bispecific antibody is isolated from the disrupted cell or the mixture using an affinity reagent.

In one embodiment, the heterodimeric bispecific antibody can be preferentially purified at specific pH range and salt concentration. In this embodiment, the heterodimeric bispecific antibody is composed of two different heavy chains, one modified at positions 40 and 47 (IMGT® numbering), or at positions 40, 45 and 47 (IMGT® numbering), on its CH1 domain; and the other one lacks modification at positions 40 and 47 (IMGT® numbering), or at positions 40, 45 and 47 (IMGT® numbering), on its CH1 domain.

In one aspect, the invention provides methods for producing multispecific antibodies, e.g., heterodimeric bispecific antigen-binding proteins, by (a) obtaining a nucleic acid sequence encoding a first immunoglobulin heavy chain comprising a first variable domain that recognizes a first epitope, wherein the first immunoglobulin heavy chain comprises an IgG1, IgG2, IgG3 or IgG4 isotype constant domain; (b) obtaining a second nucleic acid sequence encoding a second immunoglobulin heavy chain comprising a second variable domain that recognizes a second epitope, wherein the second immunoglobulin heavy chain comprises an IgG1, IgG2, IgG3 or IgG4 isotype constant domain that comprises a modification in its CH1 domain that eradicates or reduces binding to CaptureSelect® IgG-CH1 affinity reagent, or any affinity reagent targeting the human IgG1, IgG2, IgG3 and IgG4 CH1 domain; (c) obtaining a third nucleic acid sequence encoding an immunoglobulin light chain that pairs with the first and the second immunoglobulin heavy chain; (d) introducing the first, second, and third nucleic acid sequences into a mammalian cell; (e) allowing the cell to express a bispecific antibody; and (f) isolating the bispecific antibody based on the ability of the bispecific antibody to bind the CaptureSelect® IgG-CH1 affinity reagent, or any affinity reagent targeting the human IgG1, IgG2, IgG3 and IgG4 CH1 domain.

In some embodiments, the modification in the second CH1 domain comprises an S40T mutation in the IMGT® exon numbering system, a T47S mutation in the IMGT® exon numbering system or a combination thereof. In some embodiments, the first CH1 domain of the bispecific antibody, the second CH1 domain or both the first and second CH1 domains are non-immunogenic or substantially non-immunogenic in a human. In some embodiments, the bispecific antibody is isolated on a solid support comprising a Capture Select® IgG-CH1 affinity reagent, or any affinity reagent targeting the human IgG1, IgG2, IgG3 and IgG4 CH1 domain. In some embodiments, the solid support comprises a CaptureSelect® IgG-CH1 affinity column, or any affinity reagent targeting the human IgG1, IgG2, IgG3 and IgG4 CHI domain, and the bispecific antibody is isolated employing a pH gradient. In some embodiments, the pH gradient is a step gradient comprising one or more pH steps between pH 3 and pH 5.

In one aspect, the invention provides methods for isolating a bispecific antibody by isolating from a disrupted cell or a mixture of antibodies a bispecific antibody having differentially modified IgG1, IgG2, IgG3 or IgG4 CH1 domains, wherein the differentially modified CH1 domains are non-immunogenic or substantially non-immunogenic in a human, and wherein the modification results in a bispecific antibody with a heterodimeric heavy chain constant region whose monomers have a differential affinity for the CaptureSelect® IgG-CH1 affinity reagent, or any affinity reagent targeting the human IgG1, IgG2, IgG3 and IgG4 CH1 domain, and the bispecific antibody is isolated from the disrupted cell or the mixture based on its affinity for the CaptureSelect® IgG-CH1 affinity reagent, or any affinity reagent targeting the human IgG1, IgG2, IgG3 and IgG4 CH1 domain.

In some embodiments, one monomer of the heterodimeric heavy chain constant region is a human IgG1 and the other monomer of the heterodimeric heavy chain constant region is a modified human IgG1 comprising a modification selected from the group consisting an S40T mutation in the IMGT® exon numbering system, a T47S mutation in the IMGT® exon numbering system or a combination thereof. In some embodiments, the first immunoglobulin heavy chain comprises a mutation or modification altering its binding properties to an affinity chromatography resin. In some embodiments, the first immunoglobulin heavy chain comprises a mutation altering its binding properties to Protein A. In some embodiments, the first immunoglobulin heavy chain comprises a H435R mutation altering its binding properties to Protein A.

Any of the embodiments and aspects described herein can be used in conjunction with one another, unless otherwise indicated or apparent from the context. Other embodiments will become apparent to those skilled in the art from a review of the ensuing description.

BRIEF DESCRIPTION OF THE FIGURES

FIG. 1 is a table showing the specificity of the CaptureSelect® IgG-CH1 affinity reagent for known purified antibodies of different species and different isotypes.

DETAILED DESCRIPTION

Figure 2:
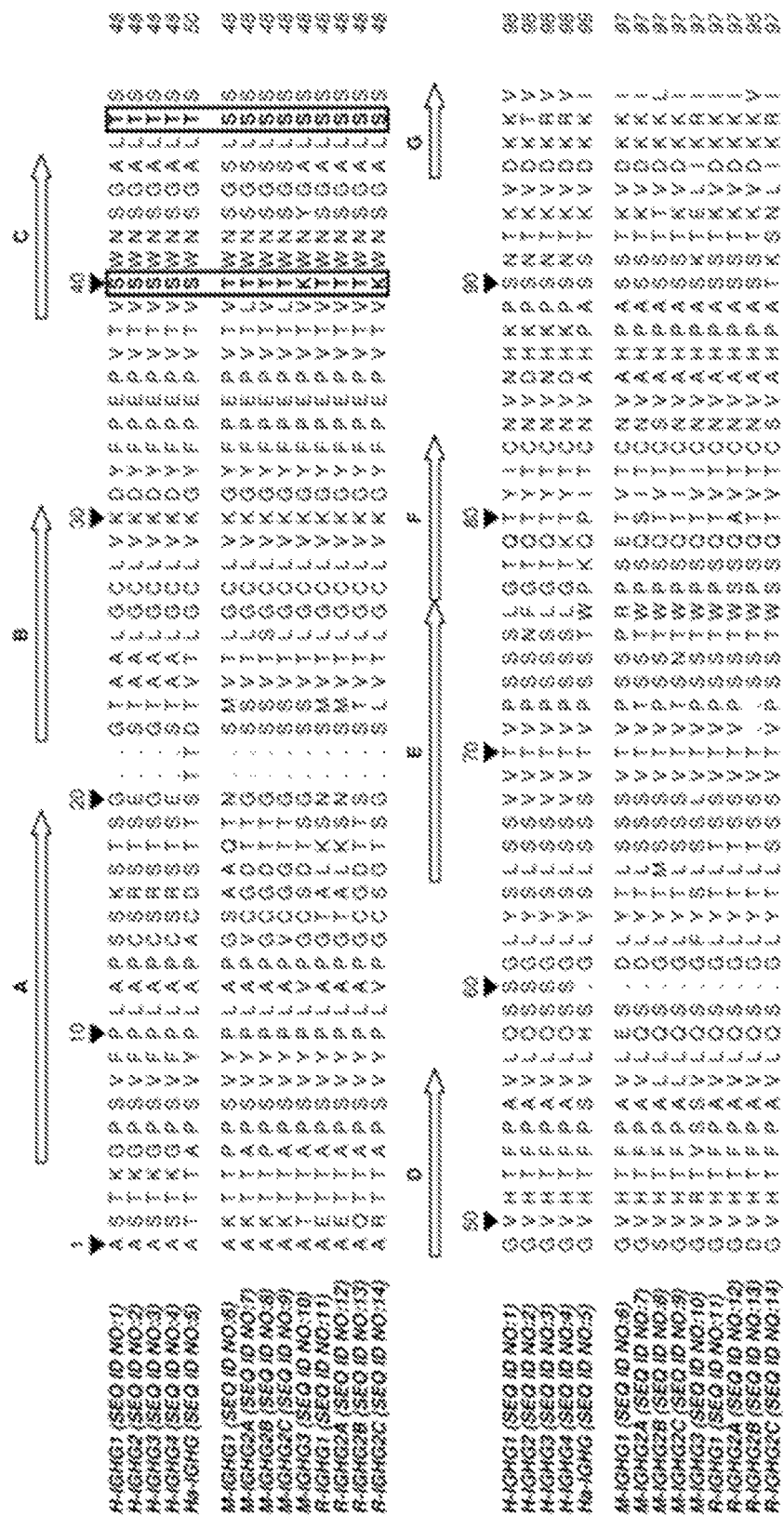
FIG. 2 is an illustration depicting the sequence alignment of the CH1 domains of the following species and isotypes: human IGHG1 (H-IGHG1, SEQ ID NO: 1), human IGHG2 (H-IGHG2, SEQ ID NO: 2), human IGHG3 (H-IGHG3, SEQ ID NO: 3), human IGHG4 (H-IGHG4, SEQ ID NO:4), hamster IGHG (Ha-IGHG, SEQ ID NO: 5), mouse IGHG1 (M-IGHG1, SEQ ID NO: 6), mouse IGHG2A (M-IGHG2A, SEQ ID NO: 7), mouse IGHG2B (M-IGHG2B, SEQ ID NO: 8), mouse IGHG2C (M-IGHG2C, SEQ ID NO: 9), mouse IGHG3 (M-IGHG3, SEQ ID NO 10), rat IGHG1 (R-IGHG1, SEQ ID NO: 11), rat IGHG2A (R-IGHG2A, SEQ ID NO: 12), rat IGHG2B (R-IGHG2B, SEQ ID NO: 13), and rat IGHG2C (R-IGHG2C, SEQ ID NO: 14).

In order to overcome the limitations of monoclonal and monovalent antibody therapeutics that can only target a single antigen or to overcome the limitations of combinations of monovalent antibody therapeutics, intense efforts have aimed at multiple antigen targeting using bispecific antibody formats. Bispecific antibodies are advantageous as they allow for multiple targeting, they increase therapeutic potential, they address redundancy of biological systems, and they provide novel mechanisms of action through abilities such as retargeting and/or increased specificity. As validated single therapeutic targets become more and more exhausted, combinations allowed by bispecific antibodies provide a new and expansive universe of targets for therapeutic agents and applications.

In recent years, efforts have been underway to develop antibody like therapeutics that have more than one antigen binding specificity, e.g., bispecific antibodies. In the case of cancer therapies, multi-specific formats could allow the possibility of using, e.g., one specificity to target the molecule to a tumor cell antigen, the other specificity to trigger a response that is not normally available to the immune system. Bispecific antibodies may also find use as surrogate ligands for two-component heterodimeric receptor systems that are normally activated by their natural ligand when it binds to and brings together both components.

Numerous formats have been developed in the art to address therapeutic opportunities afforded by molecules with multiple binding specificities. Ideally, such molecules should be well-behaved proteins that are easy to produce and purify, and possess favorable in vivo properties. e.g., pharmacokinetics appropriate for an intended purpose, minimal immunogenicity, and, if desirable, effector functions of conventional antibodies.

The most straightforward way of producing a bispecific antibody (expressing two distinct antibodies in a single cell) gives rise to multiple species, because the respective heavy chains form both homo- and heterodimers, but only the heterodimers are desired. Also, the light and heavy chains may pair inappropriately. Several examples of formats that attempt to address these problems in different ways are described below.

One format, used for Bispecific T cell Engager (BiTE) molecules (see, e.g., Wolf, E. et al. (2005) Drug Discovery Today 10:1237-1244)), is based on single chain variable fragment (scFv) modules. An scFv consists of an antibody's light and heavy chain variable regions fused via a flexible linker, which generally can fold appropriately and so that the regions can bind the cognate antigen. A BITE concatenates two scFv's of different specificities in tandem on a single chain. This configuration precludes the production of molecules with two copies of the same heavy chain variable region. In addition, the linker configuration is designed to ensure correct pairing of the respective light and heavy chains.

The BITE format has several disadvantages. First, scFv molecules are notorious for their tendency to aggregate. And although the immunogenicity of scFv linkers is reputedly low, the possibility of generating antibodies against a BITE cannot be ruled out. The absence of an Fc portion in the BITE format also makes its serum half-life very short, and this necessitates the complication of frequent repeated administrations or continuous infusion via a pump. Finally, the absence of an Fc also implies the absence of Fc-mediated effector functions, which may be beneficial in some circumstances.

A second format is a hybrid of a mouse and a rat monoclonal antibody, and relies on a modification of conventional Protein A affinity chromatography (see, e.g., Lindhofer, H. et al. (1995) J. Immunol. 155:219-225)). In this format, a mouse IgG2a and a rat IgG2b antibody are produced together in the same cell (e.g., either as a quadroma fusion of two hybridomas, or in engineered CHO cells). Because the light chains of each antibody associate preferentially with the heavy chains of their cognate species, only three distinct species of antibody can be assembled: the two parental antibodies, and a heterodimer of the two antibodies comprising one heavy/light chain pair of each, associating via their Fc portions. The desired heterodimer can be easily purified from this mixture because its binding properties to Protein A are different from those of the parental antibodies: rat IgG2b does not bind to protein A, whereas the mouse IgG2a does. Consequently, the mouse-rat heterodimer binds to Protein A but elutes at a higher pH than the mouse IgG2a homodimer, and this makes selective purification of the bispecific heterodimer possible. As with the BITE format, this hybrid format has two monovalent antigen binding sites.

The disadvantage of the mouse/rat hybrid is that because it is non-human, it is likely to provoke an immune response in the patient, which could have deleterious side effects, and/or neutralize the therapeutic.

Based on the concept described above, i.e., differential binding of a heterodimeric molecule to Protein A, other formats relying on the modification of the Fc region responsible for binding to protein A have been described in U.S. Patent Application Publication No. 20100331527A1. A limitation of engineering the Fc region of an antibody is that the mutations introduced might affect the interaction with Fc receptors and, therefore, Fc mediated functions. In particular, the FcRn interaction is crucial for long half-life of antibodies and this interaction site is located close to the Protein A binding site.

Another format, referred to as "knobs-into-holes" has been discussed in the prior art as potentially useful for the production of bispecific antibodies (U.S. Pat. No. 7,183,076). In this strategy, the Fc portions of two antibodies are engineered to give one a protruding "knob", and the other a complementary "hole." When produced in the same cell, the heavy chains are said to preferentially form heterodimers rather than homodimers, by association of the engineered "knobs" with the engineered "holes." Issues of correct light-heavy chain pairing are addressed by choosing antibodies that have different specificities but employ identical light chains.

The disadvantage of this format is that the "knobs-into-holes" strategy can result in production of a significant amount of undesirable homodimers, thus necessitating further purification steps. This difficulty is exacerbated by the fact that the contaminating species are nearly identical to the desired species in many of their properties. The engineered forms may also potentially be immunogenic, because the mutations producing the "knobs" and "holes" introduce foreign sequences.

The approach to generate bispecific antibodies described herein overcomes the disadvantages of other it does not involve mutagenesis of the Fc region but instead relies on CH1 domain modifications which alter its binding capacity to a CH1 specific affinity chromatography media. The CH1 region of antibodies is not known to be involved in interactions with receptors or other proteins and thus the effector functions and pharmacokinetic properties of the bispecific format of the invention remain unaltered. An additional benefit of some of the mutations of the CH1 domain described herein is that even very conservative changes (i.e., serine to threonine and threonine to serine) can abolish binding to the CH1 specific chromatography media. Although, these conservative mutations represent preferred changes, those ordinary skilled in the art will appreciate that less conservative mutations can also be applied for this approach.

The present invention allows for the purification of the bispecific antibody species that contains only one unmodified CH1 domain from monospecific antibodies. This can be achieved by co-expressing in a single cell two different antibody heavy chains and one antibody light chain. The two heavy chains, when paired with the common light chain mediate specific binding against two different antigens. One of the two heavy chains contains a modified CH1 domain that prevents its binding to the CH1 specific chromatography media. The co-expression of the three chains leads to the production of a mixture of three antibodies: a homodimeric monospecific antibody bearing two unmodified CH1 domains, a homodimeric monospecific antibody bearing two modified CH1 domains and a heterodimeric bispecific antibody bearing one modified CH1 domain and one unmodified CH1 domain. The differential properties of the three different molecules can exploited to efficiently purify the bispecific antibody from the monospecific ones.

The modifications of the CH1 domain described herein can be combined with other mutations or modification of a portion of an antibody, such as the Fc domain. Such combinations enable a two-step asymmetric purification approach that further facilitates isolation of the bispecific molecule.

EXAMPLES

The following examples are provided to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

The CaptureSelect® IgG-CH1 Affinity Reagent Specifically Binds To Human And Hamster IgGs Binding experiments were conducted with known purified antibodies of different species and different isotypes to test the specificity of the CaptureSelect® IgG-CH1 affinity reagent. These experiments revealed that only human and hamster IgGs could be retained on the CaptureSelect® IgG-CH1 affinity resin while mouse and rat IgGs of different isotypes couldn't bind to this affinity reagent (FIG. 1).

Example 2

Identification Of Sequence Determinants Responsible Of The IgG Binding To The CaptureSelect® IgG-CH1 Affinity Reagent Sequence alignment of human (IGHG1 SEQ ID NO: 1, IGHG2 SEQ ID NO: 2, IGHG3 SEQ ID NO: 3, IGHG4 SEQ ID NO:4), hamster (IGHG SEQ ID NO: 5), mouse (IGHG1 SEQ ID NO: 6, IGHG2A SEQ ID NO: 7, IGHG2B SEQ ID NO: 8, IGHG2C SEQ ID NO: 9, IGHG3 SEQ ID NO 10) and rat (IGHG1 SEQ ID NO: 11, IGHG2A SEQ ID NO: 12, IGHG2B SEQ ID NO: 13, IGHG2C SEQ ID NO: 14) isotypes was carried out (FIG. 2). Two residues conserved in human and hamster CH1 but not in mouse and rat sequences were identified: 40S and 47T. Their exposures to the solvent were also determined in antibody structure, indicating that these residues are highly accessible. Another residue 45A is located in the vicinity of 40S and 47T, is well exposed to the solvent and is partially conserved in the different species (FIG. 3).

Example 3

Figures 3, 4:
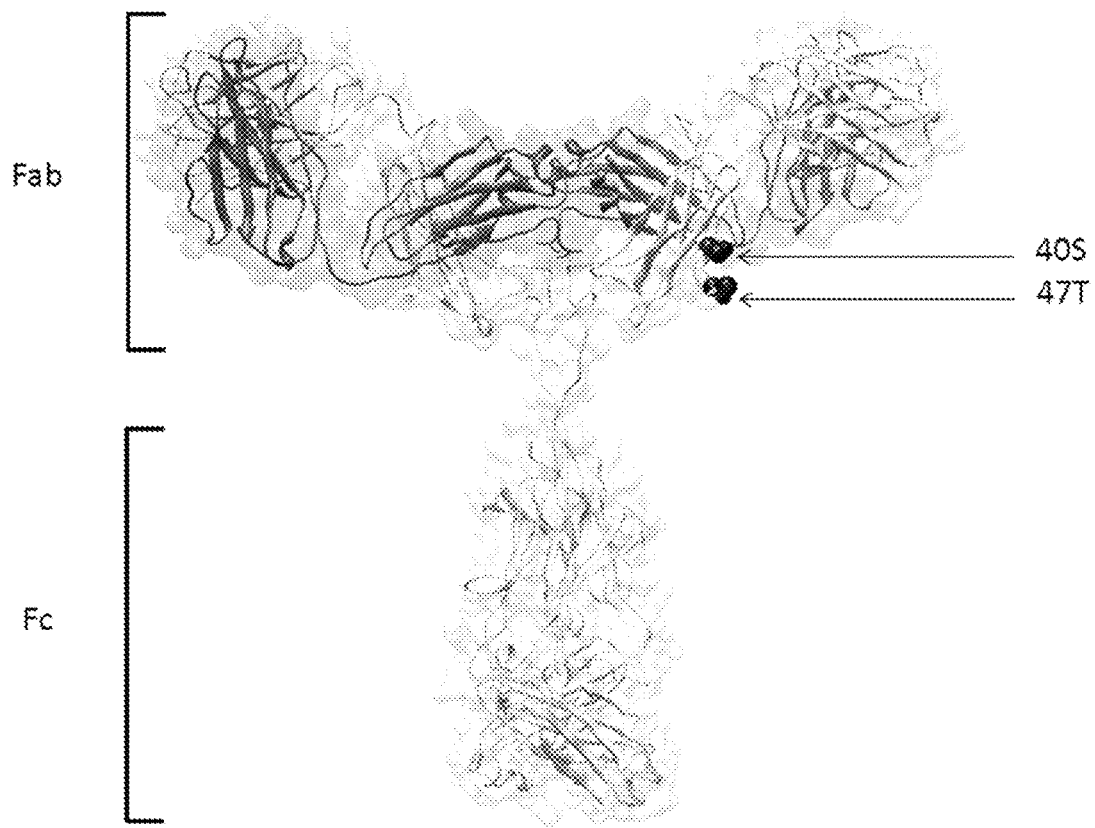
FIG. 3 is an illustration depicting an example of a bispecific antibody having wild-type CH1 domain with a serine residue at position 40 (40S) and a threonine residue at position 47 (47T).
FIG. 4 is a table depicting the CH1 domain mutations tested in the examples provided below.
Figure 5:
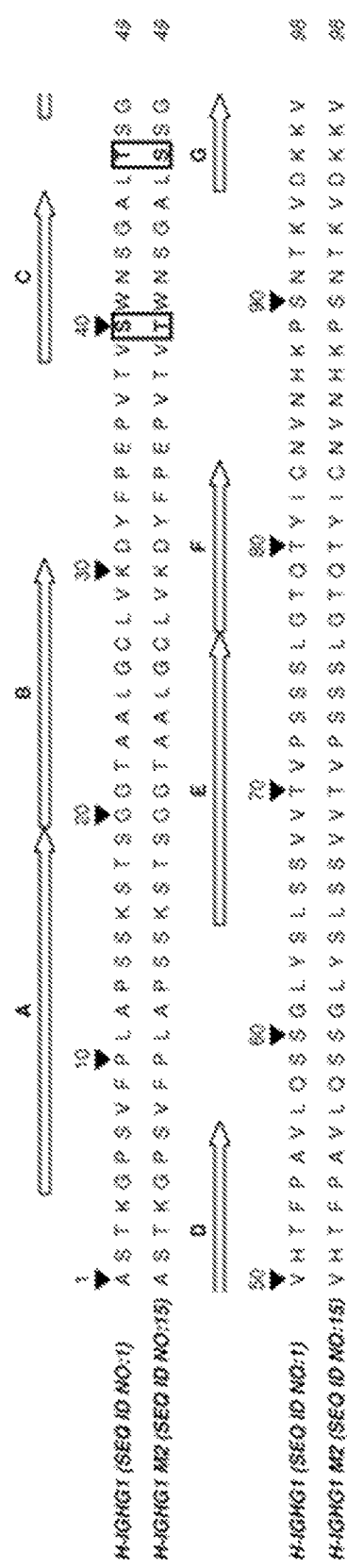
FIG. 5 is an illustration depicting the sequence alignment of the H-IGHG1 (SEQ ID NO: 1) CH1 domain and the H-IGHG1 M2 (SEQ ID NO: 15) CH1 domain, where the H-IGHG1 M2 mutant is a variant of the H-IGHG1 sequence having a threonine at position 40 (also referred to herein as an S40T mutation) and a serine at position 47 (also referred to herein as a T47S mutation).
Figure 8:
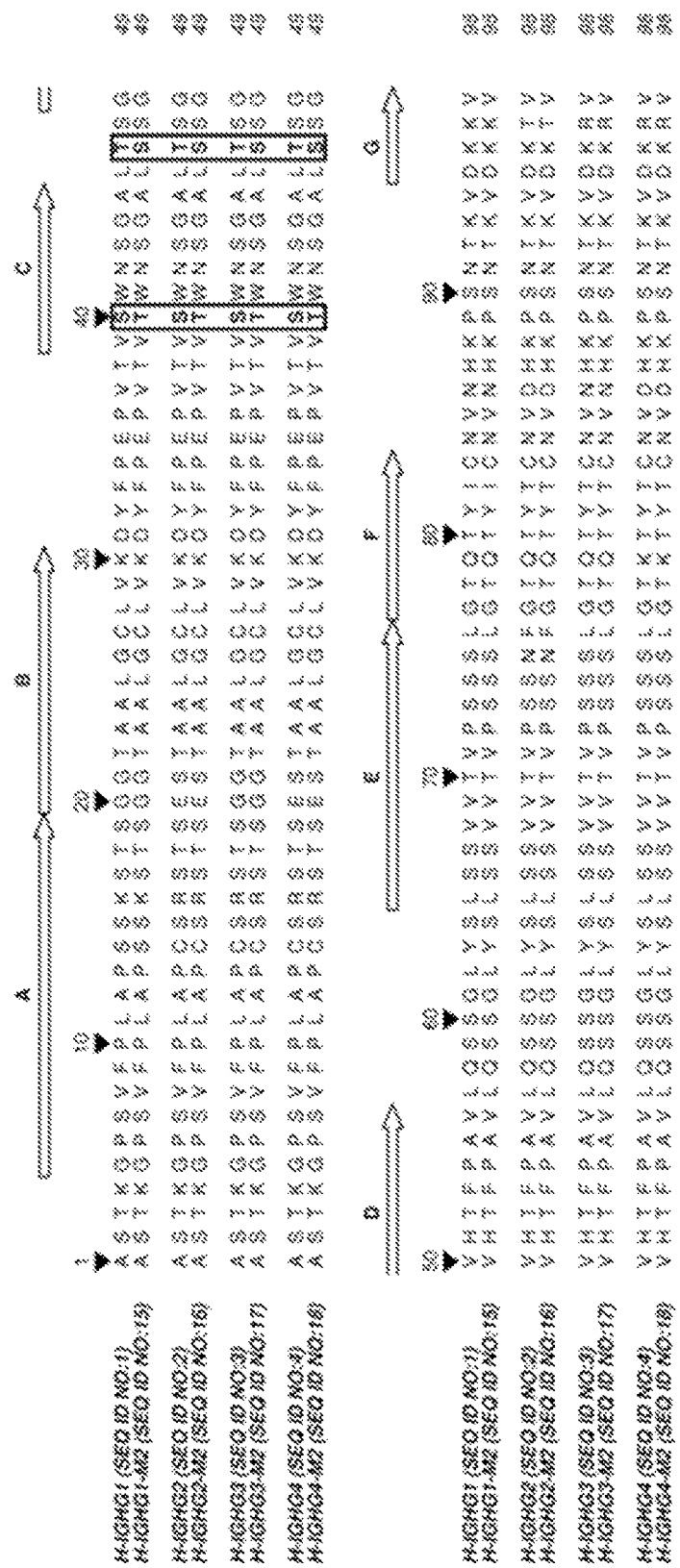
FIG. 8 is an illustration depicting the sequence alignment of the H-IGHG1 (SEQ ID NO: 1) CH1 domain and the H-IGHG1 M2 (SEQ ID NO: 15) CH1 domain; the H-IGHG2 (SEQ ID NO: 2) CH1 domain and the H-IGHG2 M2 (SEQ ID NO: 16) CH1 domain, where the H-IGHG2 M2 mutant is a variant of the H-IGHG2 sequence having a threonine at position 40 (also referred to herein as an S40T mutation) and a serine at position 47 (also referred to herein as a T47S mutation); the H-IGHG3 (SEQ ID NO: 3) CH1 domain and the H-IGHG3 M2 (SEQ ID NO: 17) CH1 domain, where the H-IGHG3 M2 mutant is a variant of the H-IGHG3 sequence having a threonine at position 40 (also referred to herein as an S40T mutation) and a serine at position 47 (also referred to herein as a T47S mutation); and the H-IGHG4 (SEQ ID NO: 4) CH1 domain and the H-IGHG4 M2 (SEQ ID NO: 18) CH1 domain, where the H-IGHG4 M2 mutant is a variant of the H-IGHG42 sequence having a threonine at position 40 (also referred to herein as an S40T mutation) and a serine at position 47 (also referred to herein as a T47S mutation).

Modification Of Human CH1 Domain To Alter Binding To CH1 Affinity Chromatography Media Modification of human IGHG1 were introduced in the CH1 domain by site-directed mutagenesis as single (S40T or T47S) double (S40T, T47S) or triple (S40T, A45S, T47S) mutations and were called M2ST, M2TS, M2 and M3, respectively (FIGS. 4, 5 and 8). These different mutants were further expressed in 293 cells using standard mammalian cell transfection procedures and purified from the supernatant as described below.

Figure 6:
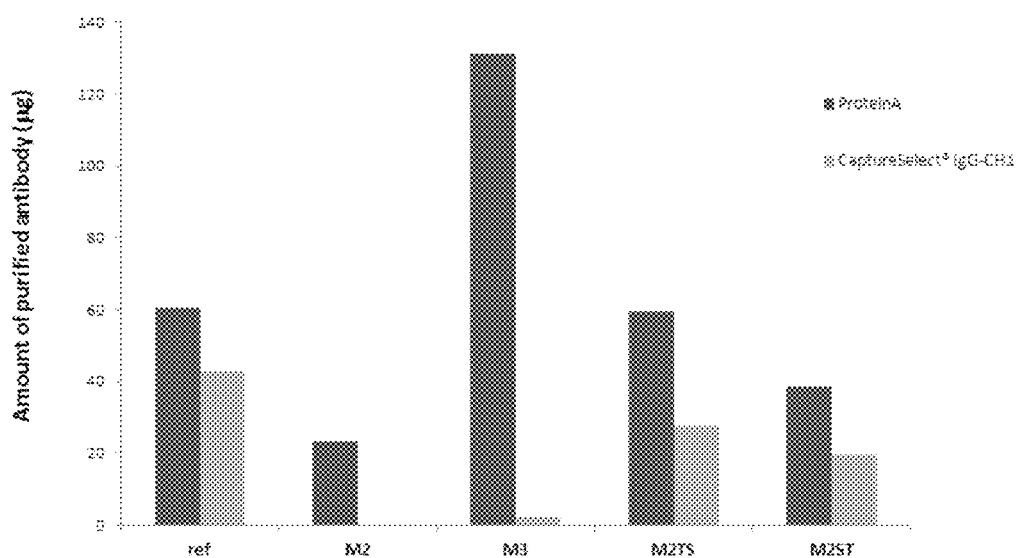
FIG. 6 is a graph depicting the amount of purified antibodies obtained after purification on either a Protein A affinity column or a CaptureSelect® IgG-CH1 affinity column.
Figure 7:
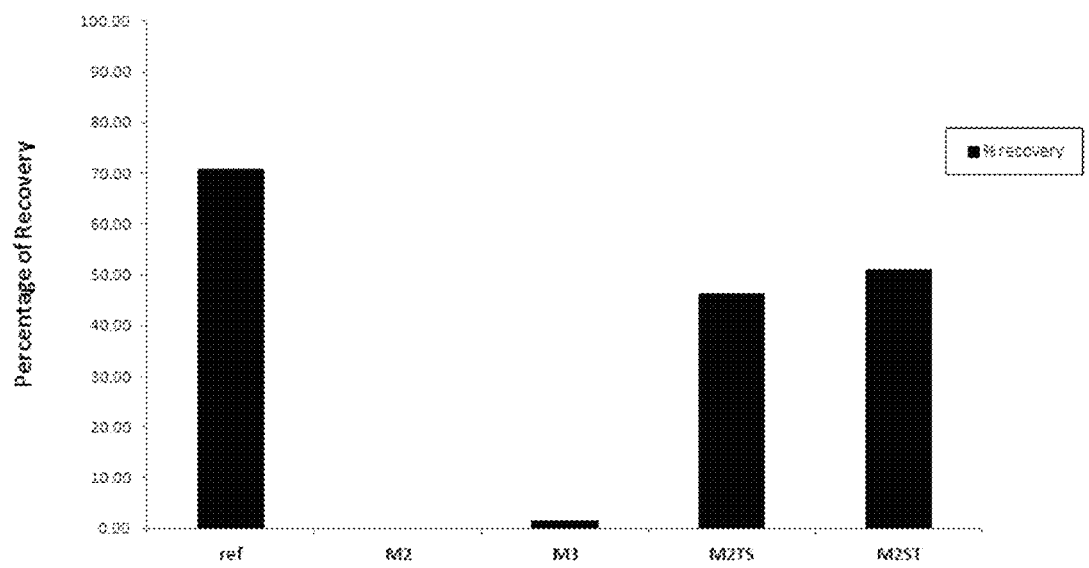
FIG. 7 is a graph depicting the percentage of purified antibody recovery using a Protein A affinity column as compared to the purified antibody recovery using a CaptureSelect® IgG-CH1 affinity column.

Protein A and CaptureSelect® IgG-CH1 purification of differentially modified IgG1: Differentially modified monomeric IgG1 (ref e.g. WT, M2ST, M2TS, M2 and M3) were expressed in 293 cells. Cell supernatants were harvested and divided in two. Antibodies were then purified either on Protein A or CaptureSelect® IgG-CH1 affinity columns. The amount of purified antibodies obtained after purification were determined (FIG. 6). Percentage of antibody recovery between Protein A and CaptureSelect® IgG-CH1 affinity columns were also calculated (FIG. 7). This percentage indicated that single mutations M2ST and M2TS lowered the antibody binding to the CaptureSelect® IgG-CH1 affinity column but didn't abrogate it. Double and triple mutants M2 and M3 recoveries on CaptureSelect® IgG-CH1 affinity column were extremely low indicating that the S40T, T47S double mutation was sufficient to abrogate IGHG1 binding to this affinity reagent.

Example 4

Generation And Purification Of An Anti-IL17 X Anti-CD3 Bispecific Antibody

It was found that two known antibodies of human IgG1 isotype, one against IL-17 and one against protein CD3, had light chains that differed by only one amino acid. Co-expression experiments revealed that the light chain of the anti-IL-17 antibody could be replaced with the light chain from the anti-CD3 antibody and still maintain high affinity binding to IL-17, thus making it feasible to produce a bispecific antibody using the anti-IL-17 heavy chain, the anti-CD3 heavy chain and the same light chain. Accordingly, the heavy chain of the anti-IL-17 antibody was modified to the M2 form (i.e., CH1 modifications S40T and T47S, by IMGT® exon numbering).

Figure 9:
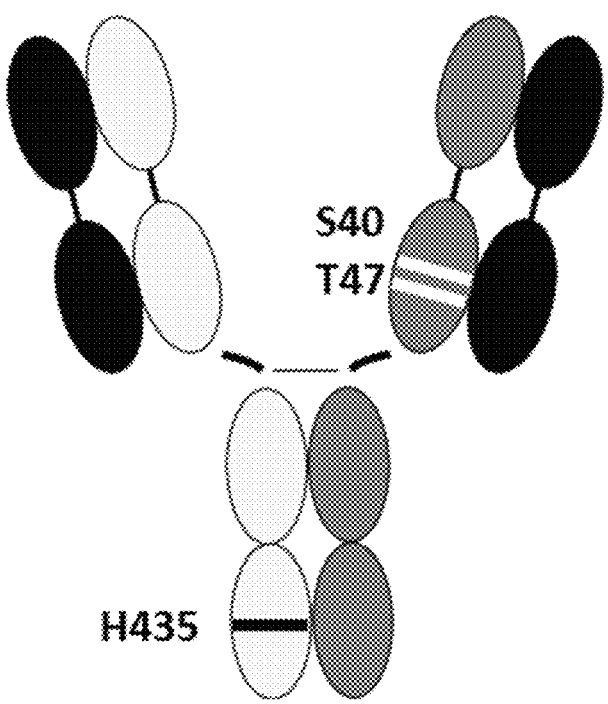
FIG. 9 is an illustration depicting a possible bispecific antibody format purified by two affinity steps. This antibody has one common light chain and two different heavy chains. Mutations have been introduced in these two different heavy chains. One heavy chains has S40T and T47S mutations in its CH1 domain which abrogate binding to CaptureSelect® IgG-CH1 affinity reagent, while the other chain has H435R mutation in its CH3 domain which abrogates binding to protein A. The positions that were mutated are indicated.
Figure 10:
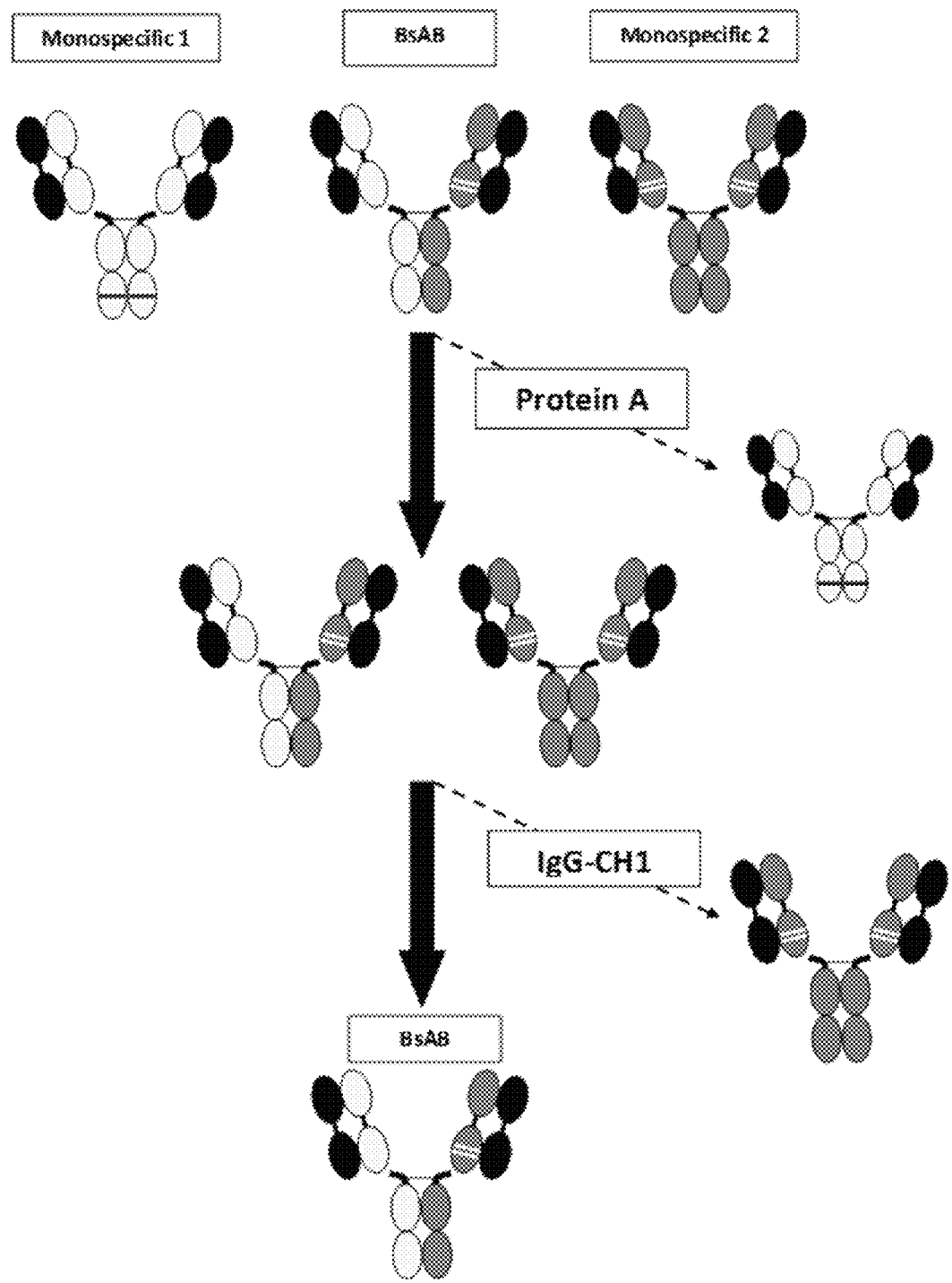
FIG. 10 is an illustration depicting the asymmetric purification strategy used to isolate bispecific antibody from the mixture of antibodies generated upon expression in single cell of two heavy chains and one light chain. The monospecific antibody carrying the H435R on both heavy chains does not bind to the Protein A resin and is lost in the flow-through. The second monospecific antibody carrying the S40T and T47S mutations on both heavy chains does not bind to the CaptureSelect® IgG-CH1 affinity reagent and is lost in the flow-through. The bispecific antibody is recovered in the final elution step.
Figure 11:
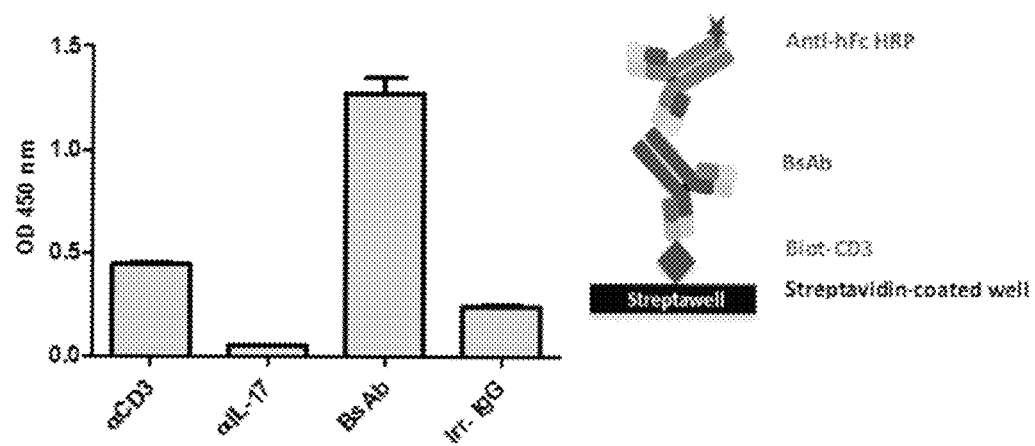
FIG. 11 is a graph depicting antibody binding results against CD3 obtained by ELISA. The ELISA format is described by a cartoon in the right panel.
Figure 12:
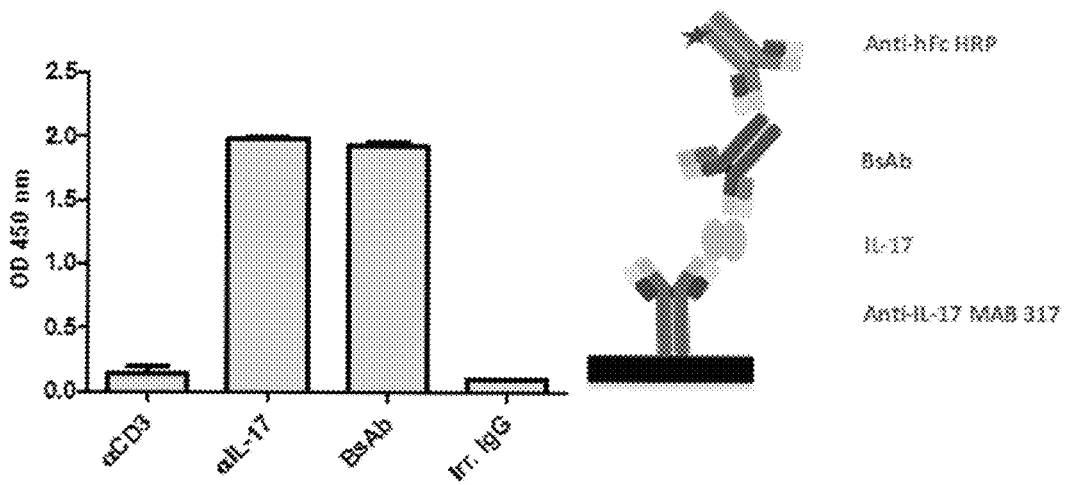
FIG. 12 is a graph depicting antibody binding results against IL-17 obtained by ELISA. The ELISA format is described by a cartoon in the right panel.
Figure 13:
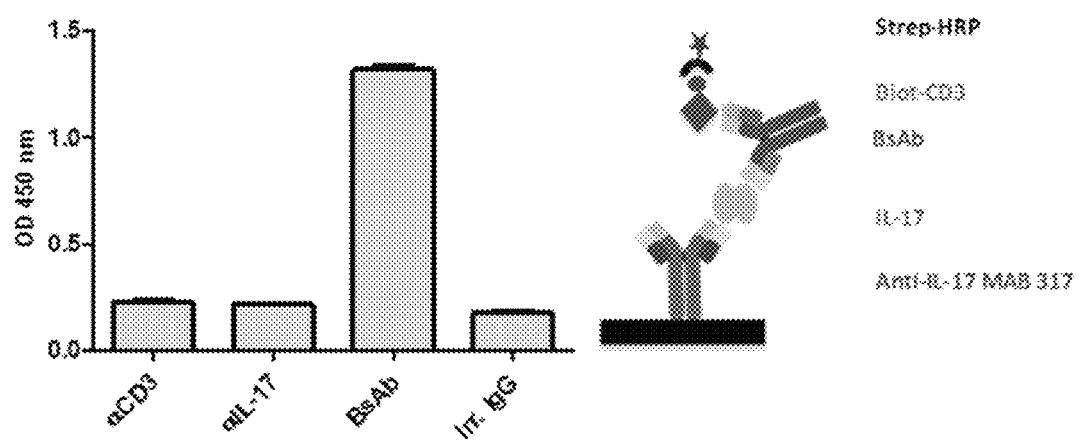
FIG. 13 is a graph depicting antibody co-engagement results against both CD3 and IL-17 obtained by ELISA. The ELISA format is described by a cartoon in the right panel.

Moreover, to facilitate the purification of the bispecific antibody, H435R mutation was introduced in the CH3 domain of the heavy chain of the anti-CD3 antibody to disrupt binding to protein A affinity reagent (FIG. 9). Based on the paper of Natsume et al. (Cancer Res 2008;68:3863-3872, the contents of which are hereby incorporated by reference in their entirety) who engineered the C-terminal part of the CH3 domain of the IgG3-Fc region to introduce binding of IgG3 to protein A, the C-terminal residues of the CH3 domain of IgG3 were introduced in human IgG1. Only two residues differ between IgG1 and IgG3 in this part of CH3 domain, which corresponds to residues His435 and Tyr436 (which are Arg and Phe residues in IgG3, respectively). After site-directed mutagenesis, H435R mutation proved to be sufficient to abrogate binding to protein A. Therefore, the anti-CD3 and anti-IL-17 heavy chains were co-expressed with the same light chain in 293 cells, and the bispecific antibody was purified from supernatant using asymmetric purification. A first purification was conducted with the protein A resin to capture bispecific antibody and anti-IL17 monospecific antibody. Then, a second purification with CaptureSelect® IgG-CH1 affinity column was used to specifically capture bispecific antibody (FIG. 10). Finally, ELISA experiments were conducted to determine the antibody binding against CD3, IL-17 or co-engagement of both CD3 and IL-17. Only, the bispecific antibody obtained by asymmetrical purification was able to engage both IL-17 and CD3 when compared to the monospecific antibodies (FIG. 11-13).

Example 5

Figure 14:
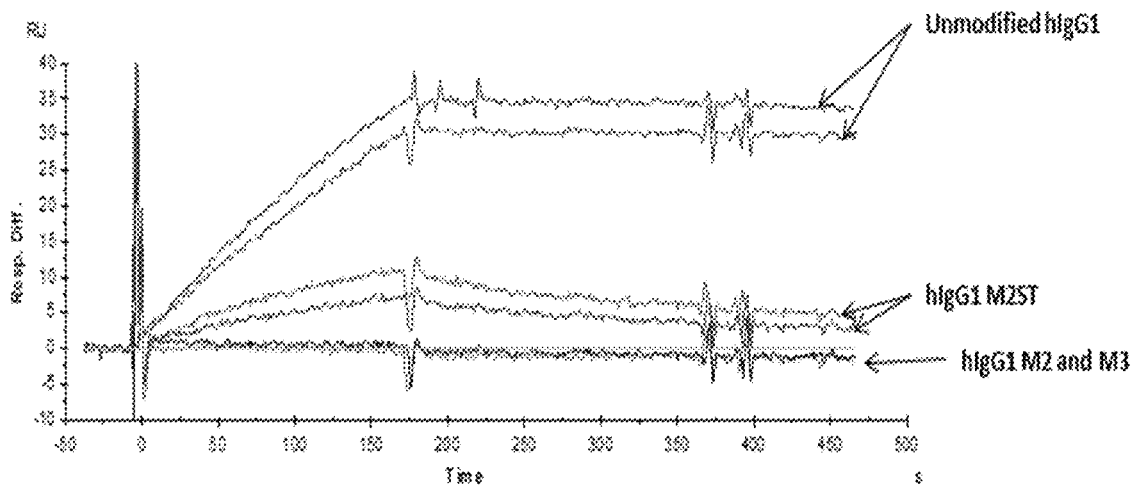
FIG. 14 is a graph depicting sensorgrams obtained on a Biacore 2000 instrument for the interaction between the biotinylated ligand of CaptureSelect® IgG-CH1 immobilized on a streptavidin coated CM5 chip, with different IgG bearing unmodified or modified CH1 domains. The mutated hIgG1 carry the mutations described in FIG. 4.

Binding Of Antibodies Containing Mutated CH1 Domains To The Ligand Of The CaptureSelect® IgG-CH1 Affinity Resin By Surface Plasmon Resonance The interaction of the IgG bearing modified and unmodified CH1 domains was characterized using surface Plasmon resonance on Biacore 2000 instrument. The biotinylated ligand of the CaptureSelect® IgG-CH1 affinity resin (BAC BV) was immobilized on a streptavidin coated CM5 chip (GE Healthcare). The M2, M3, M2ST and unmodified IgG1 were injected on the surface and the sensorgram recorded (FIG. 14). A clear interaction between the IgG containing an unmodified CH1 domain and the ligand of the CaptureSelect® IgG-CH1 affinity resin can be observed, with a very slow off rate. In contrast, the double and triple mutations present in the M2 and M3 completely abolish this interaction. The single mutation S40T leads to a partial inhibition of the interaction.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for isolating a bispecific antibody comprising:
   a) obtaining a nucleic acid sequence encoding a first immunoglobulin heavy chain comprising a first variable region that binds a first epitope, wherein the first immunoglobulin heavy chain comprises an IgG1 isotype constant domain comprising the amino acid sequence of SEQ ID NO: 1, an IgG2 isotype constant domain comprising the amino acid sequence of SEQ ID NO: 2, an Ig3 isotype constant domain comprising the amino acid sequence of SEQ ID NO: 3, or an IgG4 isotype constant domain comprising the amino acid sequence of SEQ ID NO: 4;
   b) obtaining a second nucleic acid sequence encoding a second immunoglobulin heavy chain comprising a second variable region that binds a second epitope, wherein the second immunoglobulin heavy chain comprises a second IgG1, IgG2, IgG3 or IgG4 isotype constant domain that comprises a modification in its CH1 domain that eradicates or reduces binding to an affinity reagent targeting the human IgG1, IgG2, IgG3 and IgG4 CH1 domain, wherein the second IgG1 isotype constant domain comprises the amino acid sequence of SEQ ID NO: 15 the second IgG2 isotype constant domain comprises the amino acid sequence of SEQ ID NO: 16, the second IgG3 isotype constant domain comprises the amino acid sequence of SEQ ID NO: 17, or the second IgG4 isotype constant domain comprises the amino acid sequence of SEQ ID NO: 18:

c) obtaining a third nucleic acid sequence encoding an immunoglobulin light chain that pairs with the first and the second immunoglobulin heavy chain;
d) introducing the first, second, and third nucleic acid sequences into a mammalian cell;
e) allowing the cell to express a bispecific antibody; and
f) isolating the bispecific antibody based on the ability of the bispecific antibody to bind the affinity reagent targeting the human IgG1, IgG2, IgG3 and IgG4 CH1 domain.

2. The method of claim 1, wherein the first immunoglobulin heavy chain, the second immunoglobulin heavy chain or both the first and second immunoglobulin heavy chains are non-immunogenic in a human.

3. The method of claim 1, where the bispecific antibody is isolated on a solid support an IgG-CH1 affinity column targeting the human IgG1, IgG2, IgG3 and IgG4 CH1 domain.

4. The method of claim 3, wherein the bispecific antibody is isolated employing a pH gradient.

5. The method of claim 4, wherein the pH gradient is a step gradient comprising one or more pH steps between pH 3 and pH 5.

6. The method of claim 1, wherein the first immunoglobulin heavy chain comprises a mutation altering its binding properties to Protein A.

7. The method of claim 6, wherein the mutation comprises a H435R mutation.

8. A method for isolating a bispecific antibody, comprising:
a) contacting a disrupted cell or a mixture of antibodies comprising a bispecific antibody having a differentially modified IgG1 CH1 domains with an affinity reagent targeting a human IgG1 CH1 domain, wherein the differentially modified CH1 domains are non-immunogenic in a human, wherein the differentially modified CH1 domains result in a bispecific antibody with a heterodimeric heavy chain constant region whose monomers have a differential affinity for affinity reagent targeting the human IgG1 CH1 domain, and wherein one of the monomer of the heterodimeric heavy chain constant region is a human IgG1 comprising the amino acid sequence of SEQ ID NO: 1, and the other monomer of the heterodimeric heavy chain constant region is a modified human IgG1 comprising the amino acid sequence of SEQ ID NO: 15; and
b) isolating the bispecific antibody from the disrupted cell or mixture based on the ability of the bispecific antibody to bind to the affinity reagent targeting the human IgG1 CH1 domain.

9. The method of claim 8, wherein the first immunoglobulin heavy chain comprises a mutation altering its binding properties to Protein A.

10. The method of claim 9, wherein the first immunoglobulin heavy chain comprises a H435R mutation.

* * * * *